US008914097B2

(12) United States Patent
Burlina et al.

(10) Patent No.: US 8,914,097 B2
(45) Date of Patent: Dec. 16, 2014

(54) AUTOMATED PNEUMOTHORAX DETECTION

(71) Applicant: The Johns Hopkins University, Baltimore, MD (US)

(72) Inventors: Philippe M. Burlina, N. Bethesda, MD (US); Ryan N. Mukherjee, Brookeville, MD (US)

(73) Assignee: The Johns Hopkins University, Baltimore, MD (US)

( * ) Notice: Subject to any disclaimer, the term of this patent is extended or adjusted under 35 U.S.C. 154(b) by 147 days.

(21) Appl. No.: 13/745,920

(22) Filed: Jan. 21, 2013

(65) Prior Publication Data

US 2013/0197370 A1 Aug. 1, 2013

Related U.S. Application Data

(60) Provisional application No. 61/592,285, filed on Jan. 30, 2012.

(51) Int. Cl.
| | | |
|---|---|---|
| *A61B 6/00* | (2006.01) | |
| *A61B 5/00* | (2006.01) | |
| *G06T 7/00* | (2006.01) | |
| *G06T 7/20* | (2006.01) | |
| *G06K 9/46* | (2006.01) | |
| *G06K 9/62* | (2006.01) | |

(52) U.S. Cl.
CPC ............ *A61B 5/0077* (2013.01); *G06T 7/0016* (2013.01); *G06T 7/2033* (2013.01); *G06K 9/4642* (2013.01); *G06K 9/6269* (2013.01); *G06K 9/6297* (2013.01); *G06T 2207/10016* (2013.01); *G06T 2207/10072* (2013.01); *G06T 2207/10132* (2013.01); *G06T 2207/20061* (2013.01); *G06T 2207/30061* (2013.01)
USPC ............................ 600/476; 600/407; 600/425

(58) Field of Classification Search
CPC .... G06T 7/0012; A61B 1/267; A61B 1/2676; A61B 5/08; A61B 5/11
USPC .................. 600/407, 425, 437, 476; 382/128
See application file for complete search history.

(56) References Cited

U.S. PATENT DOCUMENTS

| | | | |
|---|---|---|---|
| 5,557,687 | A | 9/1996 | Hara |
| 5,668,888 | A | 9/1997 | Doi et al. |
| 6,549,646 | B1 | 4/2003 | Yeh et al. |
| 6,577,752 | B2 | 6/2003 | Arnato, III et al. |
| 6,650,924 | B2 | 11/2003 | Kuth et al. |
| 7,431,700 | B2 * | 10/2008 | Aoki et al. .................... 600/534 |

(Continued)

FOREIGN PATENT DOCUMENTS

| | | |
|---|---|---|
| WO | 2008073560 | 6/2008 |
| WO | 2011094639 | 8/2011 |

*Primary Examiner* — Anhtuan T Nguyen
*Assistant Examiner* — Jae Woo
(74) *Attorney, Agent, or Firm* — Noah J. Hayward

(57) ABSTRACT

A method of determining the presence of a pneumothorax includes obtaining a series of frames of image data relating to a region of interest including a pleural interface of a lung. The image data includes at least a first frame and a second frame. The method further includes identifying, via processing circuitry, the pleural interface in at least the first frame and the second frame, determining, based on computing optical flow between the first and second frames, a pleural sliding classification of the image data at the pleural interface, and determining whether a pneumothorax is present in the pleural interface based on the pleural sliding classification.

11 Claims, 7 Drawing Sheets

(56) References Cited

U.S. PATENT DOCUMENTS

| | | | |
|---|---|---|---|
| 7,492,931 B2* | 2/2009 | Sabol et al. | 382/128 |
| 7,819,806 B2* | 10/2010 | Yang et al. | 600/437 |
| 7,965,869 B2 | 6/2011 | Zhou et al. | |
| 8,073,226 B2 | 12/2011 | Farag et al. | |
| 8,221,322 B2* | 7/2012 | Wang et al. | 600/437 |
| 2008/0146932 A1* | 6/2008 | Chalana et al. | 600/447 |
| 2010/0222663 A1* | 9/2010 | Wilder et al. | 600/407 |
| 2013/0018240 A1* | 1/2013 | McCoy | 600/323 |
| 2013/0039552 A1* | 2/2013 | Becker et al. | 382/128 |
| 2013/0184584 A1* | 7/2013 | Berkey | 600/441 |
| 2014/0079051 A1* | 3/2014 | Lakkis et al. | 370/350 |

* cited by examiner

AUTOMATED PNEUMOTHORAX DETECTION

CROSS-REFERENCE TO RELATED APPLICATION

This application claims priority to and the benefit of U.S. Provisional Application Ser. No. 61/592,285 filed on Jan. 30, 2012, the entire contents of which are hereby incorporated herein by reference.

TECHNICAL FIELD

Example embodiments of the present disclosure generally relate to automatic detection of lung related ailments or conditions, and more specifically relate to employment of automated image analysis to facilitate detection of pneumothoraces.

BACKGROUND

A pneumothorax is an abnormal lung condition that is characterized by the collection of air in the pleural space separating the lung from the chest wall. Pneumothoraces may occur in one or both lungs and cause a partial or complete collapse of the affected lung or lungs. The severity of the collapse of one, or sometimes both, lungs determines the oxygenation and ventilation impairment for the patient, which can lead to hemodynamic instability and/or death.

The symptoms of pneumothorax are often vague and inconclusive, so that medical imaging is required to achieve an accurate diagnosis of the condition. A trained radiologist may attempt to diagnose the existence of pneumothorax by examining chest x-rays, computed tomography (CT) scans, or ultrasound images. In fact, bedside ultrasounds have been used to accurately detect pneumothorax in acute emergency and trauma settings.

BRIEF SUMMARY

Some example embodiments include a system for automatic detection of pneumothorax based on analysis of image data of a patient's lungs. In this regard, some embodiments may enable the image data to be analyzed for sliding motion at the pleural interface. An indication of pleural sliding may indicate a lack of pneumothorax, while a lack of pleural sliding may strongly suggest the existence of a pneumothorax at the corresponding location.

In one example embodiment, a detection system is provided. The detection system may include an image sensor configured to obtain a series of frames of image data relating to a region of interest including a pleural interface of lungs and an image analyzer. The image analyzer may be in communication with the image sensor to receive the image data therefrom. The image analyzer may include processing circuitry configured to identify the pleural interface in at least a first frame of the image data and a second frame of the image data, determine, based on computing optical flow between the first and second frames, a pleural sliding classification of the image data at the pleural interface, and determine whether a pneumothorax is present in the pleural interface based on the pleural sliding classification.

In another example embodiment, a method of determining the presence of a pneumothorax is provided. The method may include obtaining a series of frames of image data relating to a region of interest including a pleural interface of lungs. The image data may include at least a first frame and a second frame. The method may further include identifying, via processing circuitry, the pleural interface in at least the first frame and the second frame, determining, based on computing optical flow between the first and second frames, a pleural sliding classification of the image data at the pleural interface, and determining whether a pneumothorax is present in the pleural interface based on the pleural sliding classification.

In another example embodiment, a computer program product comprising a computer-readable storage medium having computer-executable program code instructions stored therein is provided. The computer-executable program code instructions may include program code instructions for obtaining a series of frames of image data relating to a region of interest including a pleural interface of lungs. The image data may include at least a first frame and a second frame. The computer-executable program code instructions may further include program code instructions for identifying, via processing circuitry, the pleural interface in at least the first frame and the second frame, determining, based on computing optical flow between the first and second frames, a pleural sliding classification of the image data at the pleural interface, and determining whether a pneumothorax is present in the pleural interface based on the pleural sliding classification.

BRIEF DESCRIPTION OF THE SEVERAL VIEWS OF THE DRAWINGS

Figure 1:
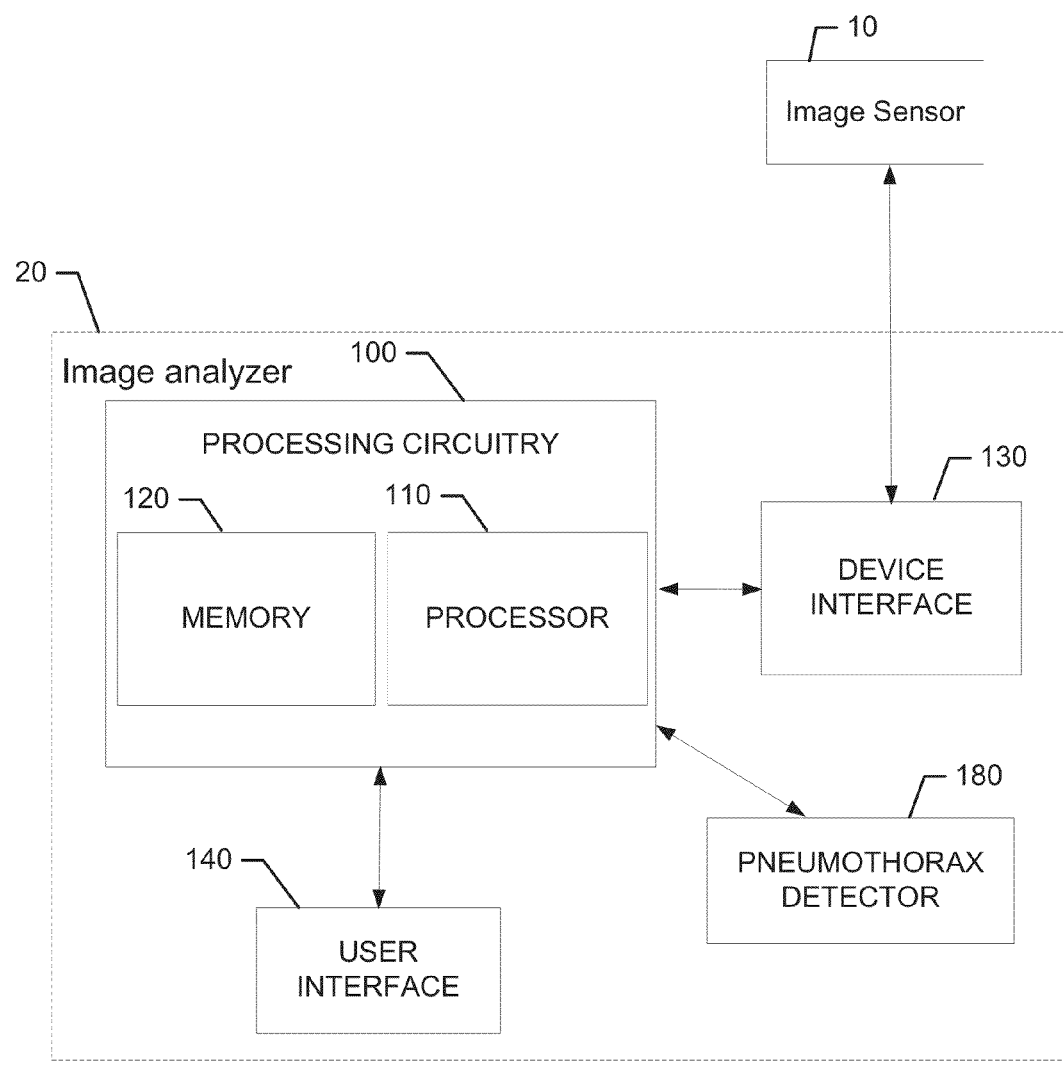
Figure 2:
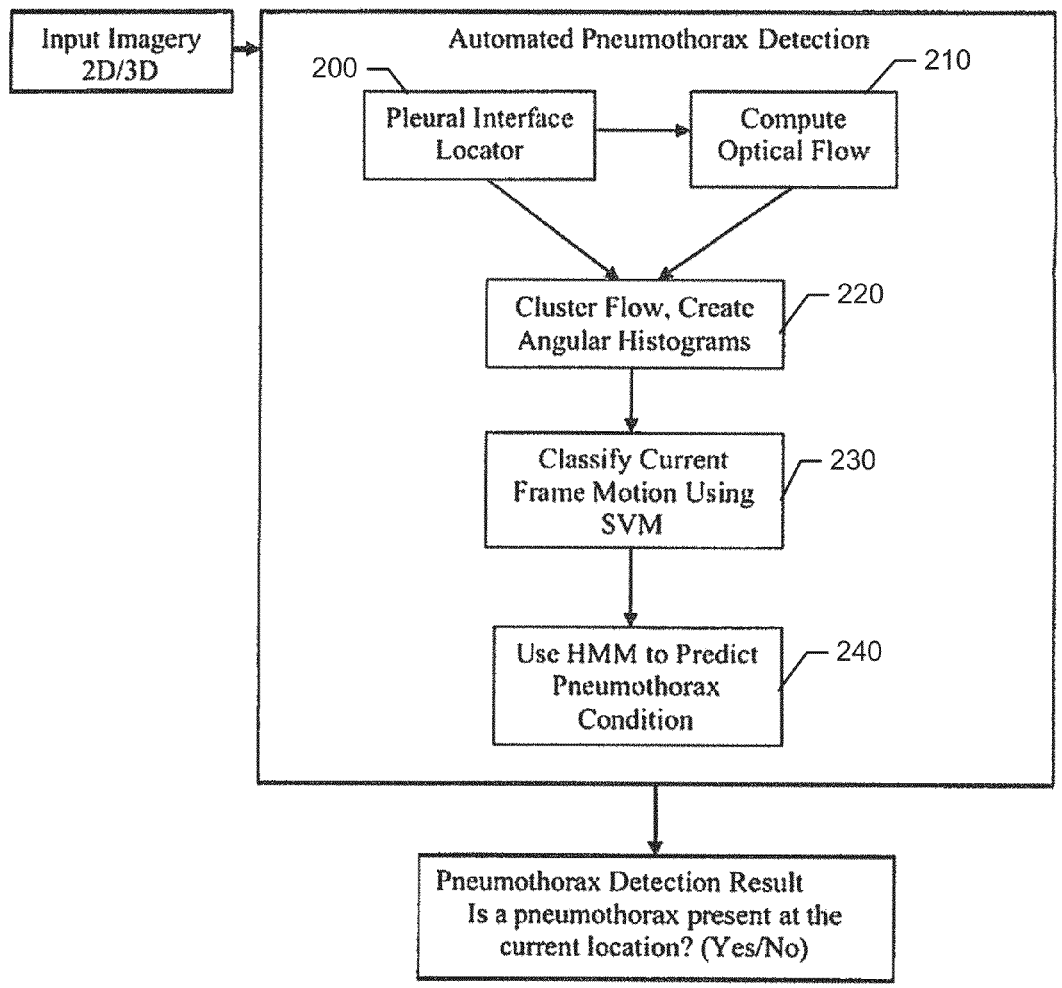
Figure 3:
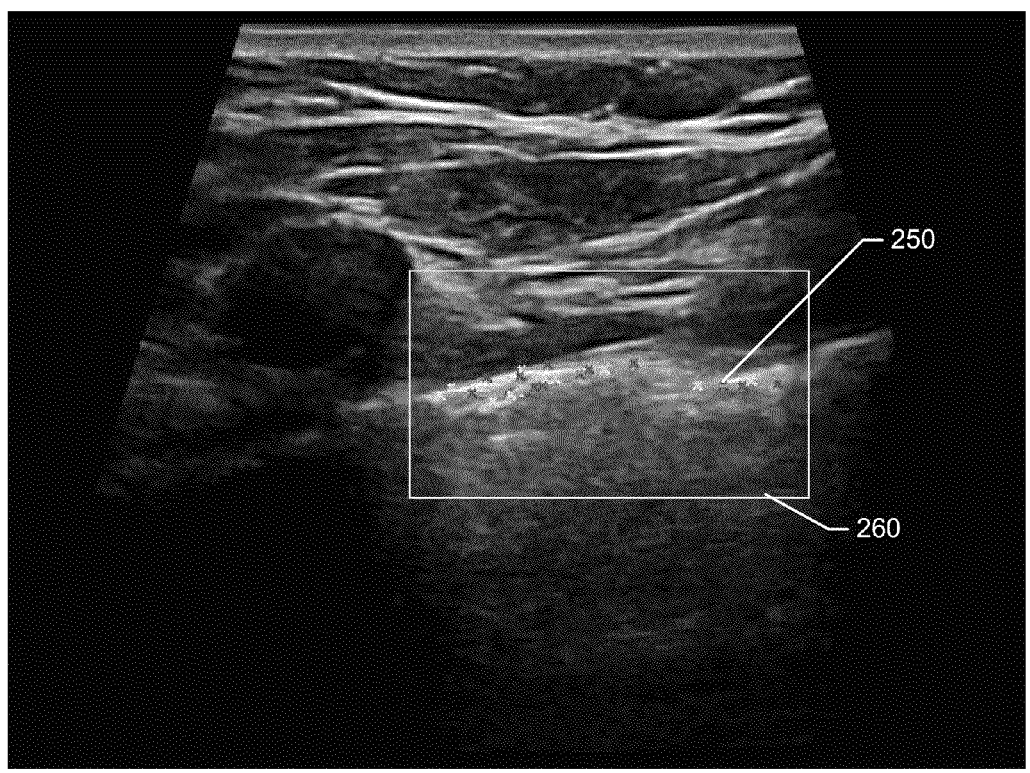
Figure 4:
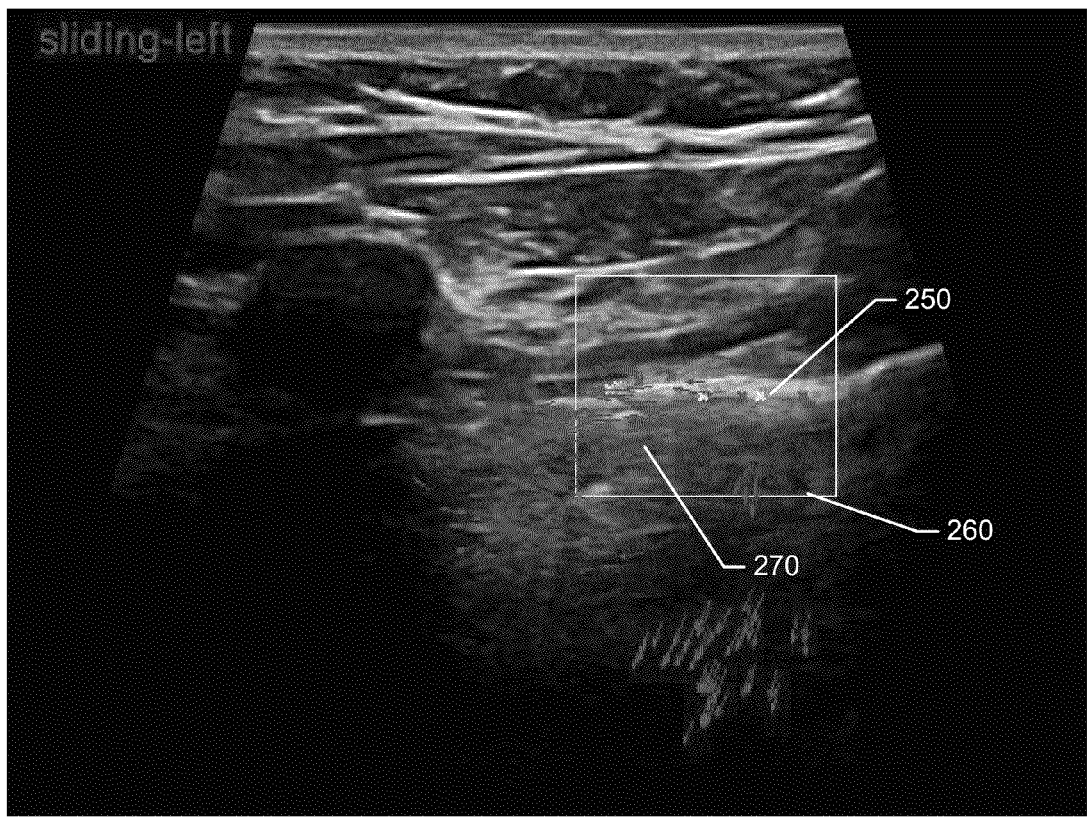
Figure 5:
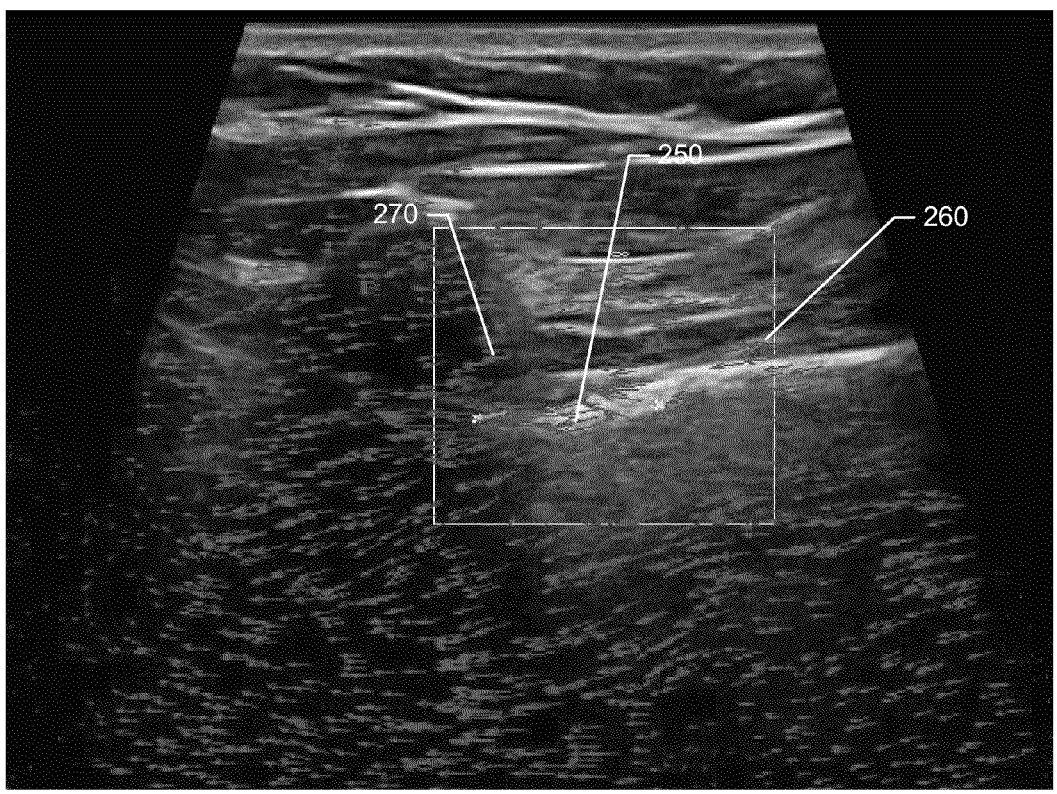
Figure 6:
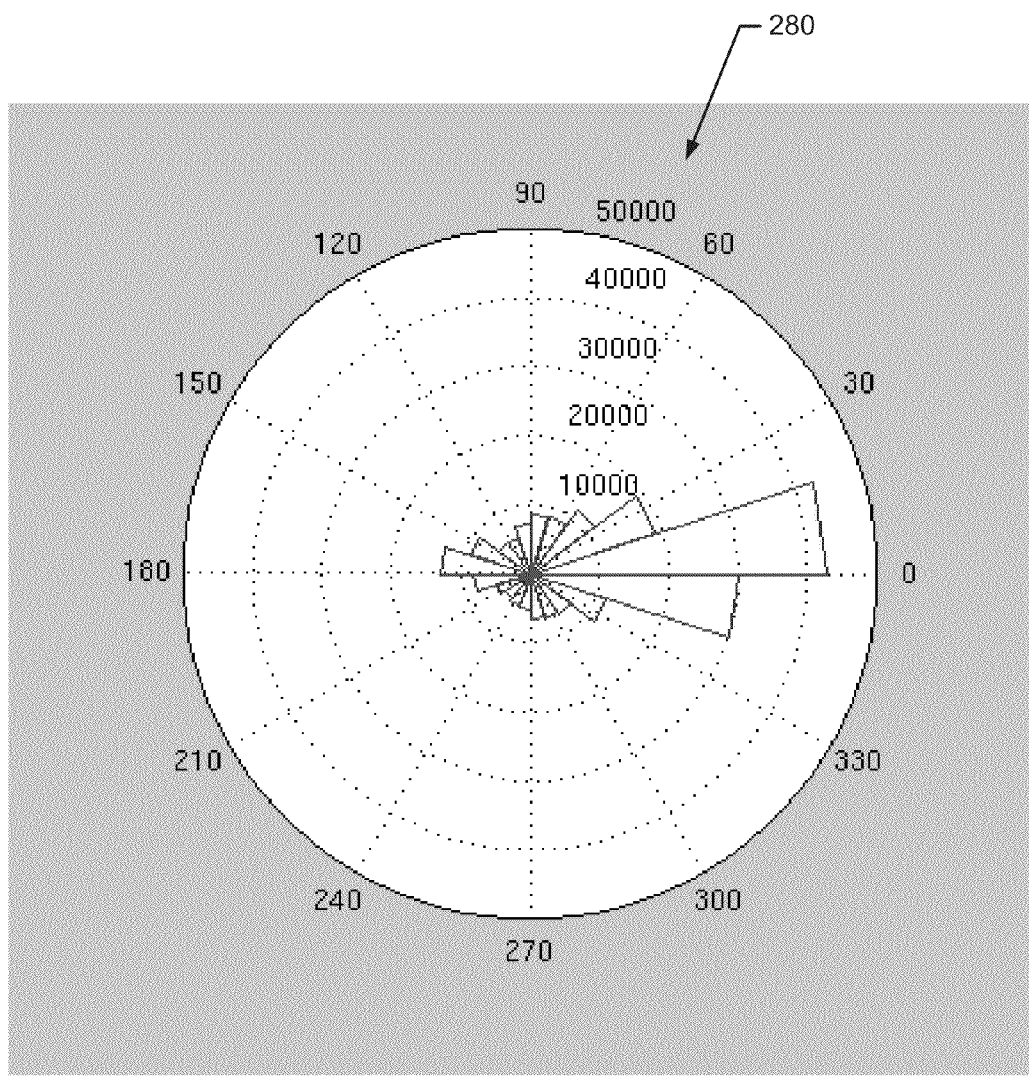
Figure 7:
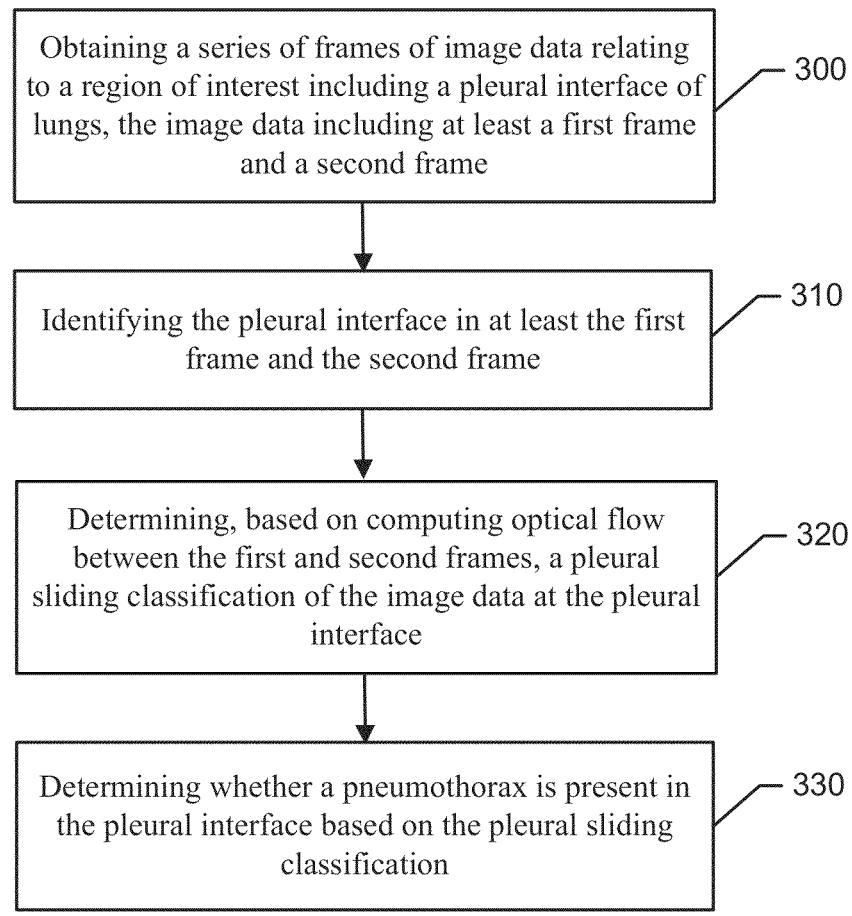

Having thus described some example embodiments of the present invention in general terms, reference will now be made to the accompanying drawings, which are not necessarily drawn to scale, and wherein:

FIG. 1 illustrates a block diagram showing one example of a detection system of an example embodiment;

FIG. 2 illustrates a block diagram of actions that a pneumothorax detector may be configured to perform in accordance with an example embodiment;

FIG. 3 illustrates an example two-dimensional ultrasound sequence. The line 250 represents Hough lines that are automatically identified as being part of the pleural line in accordance with an example embodiment;

FIG. 4 illustrates pleural line detection and sliding motion detection on a 2D ultrasound sequence according to an example embodiment;

FIG. 5 illustrates the effect of probe motion, which causes the entire image to move in a consistent direction, with slight flow differences due to simultaneous tissue motion in accordance with an example embodiment;

FIG. 6 illustrates a 20-bin angular histogram of flow vector clusters overlapping with the pleural line region according to an example embodiment; and FIG. 7 shows a block diagram of a method according to an example embodiment.

DETAILED DESCRIPTION

Some example embodiments now will be described more fully hereinafter with reference to the accompanying drawings, in which some, but not all example embodiments are shown. Indeed, the examples described and pictured herein should not be construed as being limiting as to the scope, applicability or configuration of the present disclosure. Rather, these example embodiments are provided so that this disclosure will satisfy applicable legal requirements. Like reference numerals refer to like elements throughout.

As indicated above, some example embodiments may enable the provision of a mechanism by which to diagnose pneumothorax automatically on the basis of machine executed analysis of image data of lungs. In some cases, the image data may be one-dimensional, two-dimensional or three-dimensional video imagery that may be obtained by time varying imaging modalities such as ultrasound (including Doppler ultrasound), CT or cine-MRI. The image data may be analyzed to identify or locate the pleural interface as a region of interest (ROI). The ROI may then be further analyzed to determine whether indications of pleural sliding are present in within a single image frame. Thereafter, a plurality of frames may be considered to make a determination regarding the presence of a pneumothorax.

The lungs are located in the thoracic cavity of the chest, and are essential to respiration. Each lung is somewhat triangular in shape with the apex being superior and the base being inferior. The lungs are formed of a relatively light and porous material and are maintained at a pressure that is below atmospheric pressure. The lungs are separated from the abdominal cavity by a muscular diaphragm located at the base of the lungs. The diaphragm moves to draw air into and expel air from the lungs.

The lungs are surrounded by a double-walled sac called the pleura. The pleura includes visceral and parietal pleura membranes that have a thin space between them which is referred to as a pleural cavity or pleural interface. The pleural interface normally includes a pleural fluid located therein to enable the lungs to expand and contract without adherence between the membranes. The pleural interface therefore typically enables the visceral and parietal pleura membranes to slide back and forth relative to each other during normal respiration. This phenomenon is referred to as "lung sliding". Evidence of lung sliding is considered to be evidence of normal lung function in relation to the existence of a pneumothorax. A pneumothorax is experienced by virtue of an air pocket forming in the pleural interface which may prevent lung sliding. Thus, if an absence of lung sliding can be detected in a particular region, there is a strong possibility that a pneumothorax may be occurring in the particular region.

Penetrating and blunt trauma can cause pneumothorax. Moreover, the presence of these types of top-level injuries may make it more difficult to detect the pneumothorax condition. Additionally, an initially small pneumothorax may progress into more serious states if left untreated, which may cause significant morbidity and mortality. Particularly in the fields of emergency and trauma medicine, an automatic method of detecting pneumothorax may be useful in avoiding delayed diagnosis or failures to arrive at a diagnosis relative to instances of pneumothorax. Accordingly, some example embodiments may provide a detection system that is capable of providing automatic detection of pneumothorax.

FIG. 1 illustrates a block diagram showing one example of a detection system of one example embodiment. In this example, the detection system is embodied as a computer controlled device. Thus, for example, the detection system may include an imaging sensor 10 and an image analyzer 20. The imaging sensor 10 may be an imaging device configured to obtain images of the lungs of a subject. The data collectable by the imaging sensor 10 may be captured non-invasively by obtaining image data using probes that remain external to the body, but measure radiation that passes through and/or reflects off of various body parts. In some cases, the imaging sensor 10 may generate video image data comprising a series of image frames. In an example embodiment, the image sensor 10 may be embodied as or include time varying imaging modalities such as ultrasound, CT or cine-MRI. Ultrasound in particular, may provide a relatively low cost, low power, portable modality that can be employed in emergency and trauma environments without employing ionizing radiation. However, other modalities may also be employed The imaging sensor 10 may provide image data to the image analyzer 20, which may be configured to receive and process data captured by the image sensor 10 in order to generate results that may be used to diagnose various lung conditions including pneumothorax. In some cases, the image analyzer 20 may receive the image data in real time (or near real time) directly from the image sensor 10. However, in other cases, image data from the image sensor 10 may be stored first, and may thereafter be retrieved from storage before being analyzed by the image analyzer 20.

As shown in FIG. 1, the image analyzer 20 may include or otherwise be in communication with processing circuitry 100 that is configurable to perform actions in accordance with example embodiments described herein. As such, for example, at least some of the functions attributable to the image analyzer 20 may be carried out by or otherwise instructed by the processing circuitry 100. The processing circuitry 100 may therefore provide the hardware for hosting software to configure the system for machine learning and machine driven analysis techniques consistent with example embodiments. Detection and delineation of lung conditions such as, for example, pneumothorax may then be accomplished using the processing circuitry 100.

The processing circuitry 100 may be configured to perform data processing, control function execution and/or other processing and management services according to an example embodiment of the present invention. In some embodiments, the processing circuitry 100 may be embodied as a chip or chip set. In other words, the processing circuitry 100 may comprise one or more physical packages (e.g., chips) including materials, components and/or wires on a structural assembly (e.g., a baseboard).

In an example embodiment, the processing circuitry 100 may include one or more instances of a processor 110 and memory 120 that may be in communication with or otherwise control a device interface 130 and, in some cases, a user interface 140. As such, the processing circuitry 100 may be embodied as a circuit chip (e.g., an integrated circuit chip) configured (e.g., with hardware, software or a combination of hardware and software) to perform operations described herein.

The user interface 140 (if implemented) may be in communication with the processing circuitry 100 to receive an indication of a user input at the user interface 140 and/or to provide an audible, visual, mechanical or other output to the user. As such, the user interface 140 may include, for example, a display, one or more buttons or keys (e.g., function buttons), and/or other input/output mechanisms (e.g., keyboard, microphone, speakers, cursor, joystick, lights and/or the like). The user interface 140 may display information indicating an identity or certain characteristics of a data set (e.g., including images or results of analyzing images) being processed by the image analyzer 20. The characteristics of the data set may then be processed and information associated therewith may be presented on a display of the user interface 140 based on instructions executed by the processing circuitry 100 for the analysis of the data according to prescribed methodologies and/or algorithms. Moreover, in some cases, the user interface 140 may include options for selection of one or more reports to be generated based on the analysis of a given data set.

The device interface 130 may include one or more interface mechanisms for enabling communication with other external devices (e.g., the image sensor 10) or internal functional components of the image analyzer 20. In some cases, the device interface 130 may be any means such as a device or circuitry embodied in either hardware, or a combination of hardware and software that is configured to receive and/or transmit data from/to devices in communication with the processing circuitry 100.

In an example embodiment, the memory 120 may include one or more non-transitory memory devices such as, for example, volatile and/or non-volatile memory that may be either fixed or removable. The memory 120 may be configured to store information, data, applications, instructions or the like for enabling the image analyzer 20 to carry out various functions in accordance with example embodiments of the present invention. For example, the memory 120 could be configured to buffer input data for processing by the processor 110. Additionally or alternatively, the memory 120 could be configured to store instructions for execution by the processor 110. As yet another alternative, the memory 120 may include one or more databases that may store a variety of data sets indicative of patterns, image data, feature vectors, histograms, processing algorithms and/or the like to be employed for the execution of example embodiments. Among the contents of the memory 120, applications may be stored for execution by the processor 110 in order to carry out the functionality associated with each respective application. In some cases, the applications may include directions for control of the image analyzer 20 to generate and/or employ analytical tools for analyzing image data to identify ROI and analyze data therein to determine whether a pneumothorax has occurred in the ROI. In some cases, the applications may further include directions for generating outputs and/or reports associated with analysis of patient data as described herein.

The processor 110 may be embodied in a number of different ways. For example, the processor 110 may be embodied as various processing means such as one or more of a microprocessor or other processing element, a coprocessor, a controller or various other computing or processing devices including integrated circuits such as, for example, an ASIC (application specific integrated circuit), an FPGA (field programmable gate array), or the like. In an example embodiment, the processor 110 may be configured to execute instructions stored in the memory 120 or otherwise accessible to the processor 110. As such, whether configured by hardware or by a combination of hardware and software, the processor 110 may represent an entity (e.g., physically embodied in circuitry—in the form of processing circuitry 100) capable of performing operations according to example embodiments of the present invention while configured accordingly. Thus, for example, when the processor 110 is embodied as an ASIC, FPGA or the like, the processor 110 may be specifically configured hardware for conducting the operations described herein. Alternatively, as another example, when the processor 110 is embodied as an executor of software instructions, the instructions may specifically configure the processor 110 to perform the operations described herein.

In an example embodiment, the processor 110 (or the processing circuitry 100) may be embodied as, include or otherwise control the image analyzer 20. As such, in some embodiments, the processor 110 (or the processing circuitry 100) may be said to cause each of the operations described in connection with the image analyzer 20 by directing the image analyzer 20 to undertake the corresponding functionalities responsive to execution of instructions or algorithms configuring the processor 110 (or processing circuitry 100) accordingly.

In an example embodiment, data captured in association with image scanning of the lungs of a particular patient may be stored (e.g., in the memory 120) or passed directly to the image analyzer 20. Thereafter, the data may be processed by the image analyzer 20 to enable the processing circuitry 100 to process the data in real time (or near real time) or to process the data as the data is extracted from memory. In an example embodiment, the image analyzer 20 may include a pneumothorax detector 180 that may be configured to locate the pleural interface, determine whether sliding is occurring at the pleural interface, and make a determination regarding the existence of pneumothorax based on the determination as to whether sliding is occurring.

In an example embodiment, the pneumothorax detector 180 may be any means such as a device or circuitry embodied in either hardware, or a combination of hardware and software that is configured to perform the corresponding functions of the pneumothorax detector 180 as described herein under the control of the processing circuitry 100. In an example embodiment, the pneumothorax detector 180 may be configured to perform various actions associated with determining a pneumothorax detection result relative to a particular location being examined. FIG. 2 illustrates a block diagram of some of the actions that the pneumothorax detector 180 may be configured to perform in accordance with an example embodiment. As shown in FIG. 2, the pneumothorax detector 180 may be configured to locate the pleural interface at operation 200. The pneumothorax detector 180 may also be configured to compute an optical flow for an area corresponding to the pleural interface at operation 210. Thereafter, the pneumothorax detector 180 may be configured to determine cluster flow vectors and create angular histograms at operation 220. The pneumothorax detector 180 may then be configured to classify current frame motion using a support vector machine (SVM) at operation 230 and employ a hidden Markov model (HMM) to predict a pneumothorax condition at operation 240.

In an example embodiment, operation 200 may be performed to locate the pleural line or pleural interface, which includes the parietal and visceral pleura in a normal inflated lung. Location of the pleural interface may be accomplished by combining a Hough transform, which may be used to find lines in an image, with a form of brightness thresholding in order to identify relatively bright lines in the image. Thus, for example, all lines in the image that have a brightness above a particular threshold may be identified. In some cases, after adding an additional spatial constraint to give preference to bright lines that are lower in the image (where lower means physically closer to the lungs), the pleural interface may be identified by the pneumothorax detector 180 on the basis of the bright lines that have been identified. The pleural line may be found as a continuous hyperechoic line right below the ribs. Thus, the pleural line may form the lowest bright continuous line in a typical image of the region of the lungs. Accordingly, the lines found by Hough transform may be further filtered to ensure that the lowest lines are identified as being representative of the pleural line or pleural interface. In some cases, operation 200 may be accomplished relative to each or at least a plurality of image frames.

Identification of the existence (or non-existence) of pleural sliding may be accomplished by analyzing motion of the pleural line over time based on optical flow in operation 210. Optical flow may be computed across the entirety of each image (or pairs of images) so that an iterative motion of the pleural line, as well as that of surrounding tissue (and thus also an ultrasound probe itself) may be well quantified.

Operation 210 may include a determination or computation of dense optical flow between a current frame and a previous frame based on a comparison of the current and previous frames. The computed optical flow may be employed to create a feature vector indicative of the flow. The feature vector may include a row and column of indexes of a given flow vector, as well as the optical flow vector's vector components. Clustering the resulting feature vectors using Euclidean distance may result in clusters of flow vectors that are both uniform in direction and spatially adjacent.

As such, for example, each output flow vector may be incorporated into a feature vector that includes the Cartesian coordinates of the flow vector (e.g., x and y in 2D, or x, y and z in 3D) as well as flow vector magnitudes in each direction. Those feature vectors may then be clustered as mentioned above using the Euclidean distance to form groups of flow vectors that correspond to similar locations, directions and magnitudes. Clustering the flow vectors may serve two purposes. First, clustering may allow for some additional slack in the selection of vectors that are used to identify pleural sliding. In other words, the algorithm may use features that are not within the pleural line region, but are constrained within a cluster that overlaps the pleural line region. Second, clustering may allow for the detection of translational probe motion. If the probe is translated, the entire image may contain flow vectors that agree in both direction and magnitude, which can be easily detected.

In some cases, only the clusters of flow vectors that touch the pleural line region may be used to ensure that relevant flow vectors are identified even if there are some errors in the specification of the pleural line region. Once overlapping flow vector clusters are identified, they can be aggregated into an angular histogram. In other words, as part of operation 220, angular histograms may be created using the clusters that overlap with the pleural interface region found by operation 200. The number of histogram bins required may vary in different embodiments. However, some tests have shown that an eight bin angular histogram provides relatively good performance. The angular histogram may be used to simplify the diversity of flow vector directions and magnitudes into a form that can be used to more easily identify the presence of left-sliding motion, right-sliding motion, or no motion.

In an example embodiment, operation 230 may employ a 3-class SVM that is sufficiently trained to enable the SVM to classify the resultant angular histogram according to the sliding action that is apparent. For example, the SVM may enable classification of the resultant histogram as exhibiting a particular type of sliding such as, for example, left-sliding, right-sliding, or no-sliding (e.g., not sliding) motion. In another example embodiment, the SVM can be replaced by a convolutional neural network or a Random Forest classifier. At operation 240, the classification regarding sliding action may be provided into an HMM that may be employed to use a predetermined set of state transition probabilities to form a determination as to whether the classification regarding sliding action is indicative of the presence of a pneumothorax in the pleural interface. The predetermined set of state transition probabilities may be determined by training the HMM on known data (e.g., an image sequence for which the ground truth is already known). Accordingly, using the trained HMM, temporal information associated with image frames including data covering a specific ROI including the pleural interface may be used to make a determination as to the existence of pneumothorax in the pleural interface based on whether lung sliding is evident from the temporal information.

In some embodiments, the HMM may combine multiple sliding motion observations prior to making a determination. Accordingly, the HMM may be enabled to ignore or disregard spurious motion detections by the SVM and identify only the very specific pattern of sliding motion that should be present in normal functioning lungs. In some cases, it may be useful to have the patient breathe normally or at least in a consistent fashion during the analysis. Test data has shown that, even for different breathing conditions (e.g., normal breathing, deep breathing, rapid breathing, and breath holding (with or without chest motion), example embodiments may determine pneumothorax automatically and reliably.

In some embodiments, comet tails may be detected instead of focusing directly on lung sliding. In such an example, M-mode ultrasound images may be analyzed using pattern analysis to attempt to identify comets emanating from the pleural interface. In some cases, a detection algorithm may be provided to be aware of the location of a probe (e.g., via position detection sensors or image mosaicing) and the detection algorithm may be configured to characterize partial pneumothorax. Accordingly, in some example embodiments, one dimensional, two-dimensional, or three-dimensional images taken over time may be used to supply a pattern recognition, machine vision detector that employs machine learning techniques to the identification of pneumothorax in an automated fashion.

In some cases, a detection system may receive data from (e.g., in real time or from a storage device) a sensor (e.g., image sensor 10) and process the data (e.g., via image processor 20) to generate results on a display for viewing by medical staff. In such a case, any or each of the components may be separate components that can be connected together temporarily or permanently. However, in other cases, the detection system may be a relatively small and self contained device that combines some or all of the components together into an easily portable package. Thus, for example, the detection system may be embodied as a device that may sit on, be held proximate to, or be strapped to the chest of a patient and monitoring may be conducted for pneumothorax. In this regard, for example, a relatively small bandage or adhesive strip may hold a battery powered imaging sensor forming a portion of the device (e.g., a device that may be the size of a common smart phone) proximate to the chest of the patient. The data generated may be communicated wirelessly to an analyzer, or the image analyzer may be embodied also locally at the device. In some cases, the analyzer may have a display that also provides results locally at the device. Thus, for example, a relatively small and mobile detector could be strapped to the chest of a patient and provide monitoring with minimal discomfort to the patient and without requiring active staff participation in the monitoring process. Some other related diagnostics may also be accomplished using similar techniques such as for example, determining fluid presence, heart function, heart pathologies (e.g. tachycardia, arrhythmia, etc.), or other conditions.

FIG. 3 illustrates an example two-dimensional ultrasound sequence. The line 250 represents Hough lines that are automatically identified as being part of the pleural line. The box 260 denotes the region (or ROI) over which overlapping flow clusters may be found in accordance with an example embodiment. FIG. 4 illustrates pleural line detection and sliding motion detection on a 2D ultrasound sequence according to an example embodiment. In FIG. 4, box 260 and line 250 are shown, but flow vectors 270 are also shown to indicate flow vectors included within flow vector clusters, as described above, that overlapped the pleural line region. The output of an SVM sliding motion classification operation (e.g., sliding-left) is also shown at the top left of this image. FIG. 5 illustrates the effect of probe motion, which causes the entire image to move in a consistent direction, with slight flow differences due to simultaneous tissue motion. The pleural line is detected and a majority of the flow vectors are clustered into the same cluster, which overlaps the pleural line region. In this case, it is possible to identify probe motion and prevent it from affecting the pneumothorax detection algorithm. FIG. 6 illustrates a 20-bin angular histogram 280 of flow vector clusters overlapping with the pleural line region according to an example embodiment. This histogram may correlate to a pair of 2D ultrasound images that exhibited right pleural sliding motion, which corresponds well with the large bin values pointing in the zero degree direction.

FIG. 7 is a flowchart of a method and program product according to an example embodiment of the invention. It will be understood that each block of the flowchart, and combinations of blocks in the flowchart, may be implemented by various means, such as hardware, firmware, processor, circuitry and/or other device associated with execution of software including one or more computer program instructions. For example, one or more of the procedures described above may be embodied by computer program instructions. In this regard, the computer program instructions which embody the procedures described above may be stored by a memory device of a user terminal and executed by a processor in the user terminal. As will be appreciated, any such computer program instructions may be loaded onto a computer or other programmable apparatus (e.g., hardware) to produce a machine, such that the instructions which execute on the computer or other programmable apparatus create means for implementing the functions specified in the flowchart block(s). These computer program instructions may also be stored in a computer-readable memory that may direct a computer or other programmable apparatus to function in a particular manner, such that the instructions stored in the computer-readable memory produce an article of manufacture which implements the functions specified in the flowchart block(s). The computer program instructions may also be loaded onto a computer or other programmable apparatus to cause a series of operations to be performed on the computer or other programmable apparatus to produce a computer-implemented process such that the instructions which execute on the computer or other programmable apparatus implement the functions specified in the flowchart block(s).

Accordingly, blocks of the flowchart support combinations of means for performing the specified functions and combinations of operations for performing the specified functions. It will also be understood that one or more blocks of the flowchart, and combinations of blocks in the flowchart, can be implemented by special purpose hardware-based computer systems which perform the specified functions, or combinations of special purpose hardware and computer instructions.

In this regard, a method of determining the presence of a pneumothorax according to an example embodiment of the invention is shown in FIG. 7. The method of FIG. 7 may entirely, or at least in part, be executed automatically (e.g., without operator interaction to initiate each step or the series of steps) by processing circuitry. The method may include obtaining a series of frames of image data relating to a region of interest including a pleural interface of lungs at operation 300. The image data may include at least a first frame and a second frame. The method may further include identifying the pleural interface in at least the first frame and the second frame at operation 310, determining, based on computing optical flow between the first and second frames, a pleural sliding classification of the image data at the pleural interface at operation 320, and determining whether a pneumothorax is present in the pleural interface based on the pleural sliding classification at operation 330.

In some embodiments, additional optional operations may be included or the operations described above may be modified or augmented. Each of the additional operations, modification or augmentations may be practiced in combination with the operations above and/or in combination with each other. Thus, some, all or none of the additional operations, modification or augmentations may be utilized in some embodiments. In an example embodiment, determining the pleural sliding classification may include determining the pleural sliding classification based on clustering of feature vectors indicative of the optical flow based on Euclidean distance to generate clusters that are uniform in direction and spatially adjacent. In some cases, determining the pleural sliding classification may further include employing angular histograms that overlap with the pleural interface of the region of interest using clusters generated by the clustering of the feature vectors. In some cases, a trained SVM may be employed to classify the angular histograms and the angular histograms may be classified as left-sliding, right-sliding or no-sliding. In an example embodiment, identifying the pleural interface may include combining a Hough transform that finds lines in the first and second frames of the image data with brightness thresholding to identify bright lines in the first and second frames of the image data to identify the pleural interface. This may include employing a spatial constraint giving preference to bright lines closer to the lungs to locate the pleural interface. The image sensor may be configured to obtain one-dimensional, two-dimensional or three-dimensional video imagery of the lungs as the image data. In an example embodiment, determining whether the pneumothorax is present in the pleural interface may include employing a HMM to analyze the pleural sliding classification relative to a predetermined set of state transition probabilities. The predetermined set of state transition probabilities may be determined by training the HMM on an image sequence of known data.

Many modifications and other embodiments of the inventions set forth herein will come to mind to one of ordinary skill in the art to which these inventions pertain, having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Moreover, although the foregoing descriptions and the associated drawings describe example embodiments in the context of certain combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. In cases where advantages, benefits or solutions to problems are described herein, it should be appreciated that such advantages, benefits and/or solutions may be applicable to some example embodiments, but not necessarily to all example embodiments. Thus, any advantages, benefits or solutions described herein should not be thought of as being critical, required or essential to all embodiments or to that which is claimed herein. Although specific terms are employed herein, they are used in a generic and descriptive sense only and not for purposes of limitation.

What is claimed is:

1. A detection system comprising:
   an image sensor configured to obtain image data relating to a region of interest including a pleural interface of a lung; and
   an image analyzer in communication with the image sensor to receive the image data therefrom, the image analyzer including processing circuitry configured to:
   identify the pleural interface in at least a first frame of the image data and a second frame of the image data;
   determine, based on computing optical flow between the first and second frames, a pleural sliding classification of the image data at the pleural interface; and
   determine whether a pneumothorax is present in the pleural interface based on the pleural sliding classification.

2. The detection system of claim 1, wherein the processing circuitry is configured to determine the pleural sliding classification based on clustering of feature vectors indicative of the optical flow based on Euclidean distance to generate clusters that are uniform in direction and spatially adjacent.

3. The detection system of claim 2, wherein the processing circuitry is configured to determine the pleural sliding classification by employing angular histograms that overlap with the pleural interface of the region of interest using clusters generated by the clustering of the feature vectors.

4. The detection system of claim 3, wherein the processing circuitry is configured to determine the pleural sliding classification by employing a trained support vector machine to classify the angular histograms.

5. The detection system of claim 4, wherein the processing circuitry is configured to classify the angular histograms as one of left-sliding, right-sliding and no-sliding to determine the pleural sliding classification.

6. The detection system of claim 1, wherein the processing circuitry is configured to combine a Hough transform that finds lines in the first and second frames of the image data with brightness thresholding to identify bright lines in the first and second frames of the image data to identify the pleural interface.

7. The detection system of claim 6, wherein the processing circuitry is further configured to employ a spatial constraint giving preference to bright lines closer to the lungs to locate the pleural interface.

8. The detection system of claim 1, wherein the image sensor is configured to obtain one of one-dimensional video imagery, two-dimensional video imagery and three-dimensional video imagery of the lungs as the image data.

9. The detection system of claim 1, wherein the image sensor is provided in a device that is attachable externally to a chest of a patient.

10. The detection system of claim 1, wherein the processing circuitry is configured to determine whether the pneumothorax is present in the pleural interface by employing a hidden Markov model to analyze the pleural sliding classification relative to a predetermined set of state transition probabilities.

11. The detection system of claim 10, wherein the predetermined set of state transition probabilities is determined by training the hidden Markov model on an image sequence of known data.

* * * * *